United States Patent
Huggins et al.

(10) Patent No.: US 7,051,457 B1
(45) Date of Patent: May 30, 2006

(54) FORMFITTING PROTECTIVE FOOTWEAR APPARATUS

(76) Inventors: Jamie J. Huggins, 331 Harvard St., Apt. 1, Cambridge, MA (US) 02139; Nicole T. Huggins, 331 Harvard St., Apt. 1, Cambridge, MA (US) 02139

( * ) Notice: Subject to any disclaimer, the term of this patent is extended or adjusted under 35 U.S.C. 154(b) by 0 days.

(21) Appl. No.: 09/557,029

(22) Filed: Apr. 20, 2000

Related U.S. Application Data

(60) Provisional application No. 60/130,122, filed on Apr. 20, 1999.

(51) Int. Cl.
  *A43B 1/10* (2006.01)
  *A43B 1/12* (2006.01)
  *A43B 5/12* (2006.01)
  *A41D 1/08* (2006.01)
  *A61F 13/00* (2006.01)

(52) U.S. Cl. .................. 36/4; 36/7.4; 36/8.3; 2/238; 602/61; 602/77

(58) Field of Classification Search .............. 36/4, 36/8.1, 94, 112, 7.3, 77 R, 26, 9 R, 11.5, 36/7.1 R, 7.2, 7.4, 7.5, 77 M, 8.3, 71; 2/239–242; 602/3, 65, 77, 60–63, 30
See application file for complete search history.

(56) References Cited

U.S. PATENT DOCUMENTS

| | | | | | |
|---|---|---|---|---|---|
| 1,074,595 | A | * | 10/1913 | Aumont | 36/8.1 |
| 3,334,356 | A | * | 8/1967 | Abel | 2/239 |
| 3,967,390 | A | * | 7/1976 | Anfruns | 36/94 |
| 4,069,600 | A | * | 1/1978 | Wise | 2/239 |
| 4,277,897 | A | * | 7/1981 | O'Connell | 36/7.2 |
| 4,294,022 | A | * | 10/1981 | Stockli et al. | 36/9 R |
| 4,495,715 | A | * | 1/1985 | Frederickson et al. | 36/7.1 R |
| 4,651,354 | A | * | 3/1987 | Petrey | 2/239 |
| 5,554,107 | A | * | 9/1996 | Shannahan | 602/62 |
| 5,617,585 | A | * | 4/1997 | Fons et al. | 2/239 |
| 5,682,617 | A | * | 11/1997 | Tumas | 2/239 |
| 5,774,898 | A | * | 7/1998 | Malpee | 2/239 |
| 6,041,443 | A | * | 3/2000 | Pas et al. | 2/239 |
| 6,044,497 | A | * | 4/2000 | Richardson | 36/77 R |

* cited by examiner

*Primary Examiner*—Anthony Stashick
(74) *Attorney, Agent, or Firm*—Amster, Rothstein & Ebenstein LLP

(57) ABSTRACT

A formfitting protective footwear apparatus comprising, generally, a protective sheath that envelops all or a portion of the foot from the ankle forward. In all embodiments, the formfitting protective footwear apparatus of the present invention surrounds the forefoot about the instep and arch and extends forward to protect at least the ball of the foot.

7 Claims, 7 Drawing Sheets

FORMFITTING PROTECTIVE FOOTWEAR APPARATUS

This application claims the benefit of Provisional Application No. 60/130,122, filed Apr. 20, 1999.

FIELD OF THE INVENTION

The present invention relates to protective footwear for use in dance, athletic, and other activities.

BACKGROUND OF THE INVENTION

The need for protective and functional footwear intended for specific applications is well-known. Just as basketball and football place different demands on the human foot and thus require different footwear, different forms of dance and athletics also require specialized footwear. For example, balletic dance requires specially designed toe shoes, jazz dance requires specially designed character shoes, and tap dance requires specially modified tap shoes. Until now, however, there has been no satisfactory footwear for use by modern dancers, despite the fact that modern dance places severe stresses on the human foot.

Unlike many more traditional forms of dance, modern dance requires rapid, abrupt, and complex shifts in body position, center of gravity, directional momentum, and weight distribution. Included in these movements are forceful turns, spins, and other such movements that can cause friction burns, tearing, slivers, blisters, and other foot problems. In addition, modern dancers—like other dancers—risk serious injury if their foot should slip on the dance floor or if they should turn their ankle. However, given the aesthetic requirements of their art, most modern dancers currently opt to dance barefoot and tolerate the damage done to their feet.

Earlier, unsuccessful attempts at providing such footwear range from the use of thongs that were wrapped around the foot to dancers cutting up nylon stockings and tying them to their feet before each performance. The only footwear currently available for use in modern dance comprises a "sole" that is secured to the foot by means of an ankle strap and toe loops. However, because this sole is not securely bound to the sole of the foot, severe tearing of the skin is common, particularly between the great and index toes. For that reason, most modern dancers do not use this apparatus. A major drawback of all the above approaches is that such footwear does not provide all of the protective and safety benefits desired, nor are they durable and minimally disruptive to a dancer's performance.

The ideal modern dance footwear would both protect the feet from friction burns, tearing, slivers, blisters, and other foot problems and also provide beneficial traction, optional ankle support, and other safety benefits. In addition to providing these advantages, the ideal modern dance footwear should be an unobtrusive article that either gives the appearance of a naked foot or that coordinates with a dance costume. It should be durable, reusable, and, ideally, washable, yet not impede a dancer's performance.

In additional contemplated embodiments, the footwear article of the present invention may be modified for use in the martial arts, where training involves many of the same movements as modern dance and where difficult surfaces, such as wooden, ceramic, or synthetic gymnasium floors, must be used. The footwear of the present invention may also be adapted for use in aquatic and marine environments, particularly for uses that require surefooted performance and foot protection, such as sailing, surfing, and sailboarding, without the disadvantages of shoes and other footwear.

The present invention provides an elegant solution to all of these problems.

SUMMARY OF THE INVENTION

Accordingly, it is an object of the present invention to provide a footwear article that is capable of accommodating rapid, abrupt, and complex shifts in body position, center of gravity, directional momentum, and weight distribution without causing friction burns, tearing, slivers, blisters, and other foot problems, yet does not restrict the foot in its movement or provide the appearance of a shod foot.

It is another object of the present invention to provide a footwear article that provides beneficial traction, optional ankle support, and other safety benefits.

It is a further object of the present invention to provide a footwear article that is unobtrusive and that either gives the appearance of a naked foot or that coordinates with a costume.

It is an additional object of the present invention to provide a footwear article that is durable, reusable, and, ideally, washable, yet that does not interfere with the wearer's performance.

It is a still further object of the present invention to provide a footwear article that is suitable for use in the martial arts.

It is yet another object of the present invention to provide a footwear article that is suitable for use in an aquatic or marine environment.

The present invention is an article of footwear that comprises, generally, a protective sheath that envelops all or a portion of the foot from the ankle downward. In all embodiments, the formfitting protective footwear apparatus of the present invention surrounds the forefoot about the instep and arch and extends forward to protect at least the ball of the foot. The footwear of the present invention is intended primarily for use by modern dancers, although other embodiments suitable for other uses, such as in martial arts training, sailing surfing, and sailboarding, are contemplated.

Prior to this invention, only ineffective and/or unreliable devices were available to the modern dancer. In addition to failing to adequately protect the foot, such devices were not durable and did not provide the desired safety benefits of the present invention. The significance of the present invention is that it enables a modern dancer to perform difficult movements with force and confidence that they will not injure their feet or other portions of their body as a result. These benefits extend to other users of the present invention, such as martial artists, sailors, surfers, and sailboarders.

Further objects and advantages of the invention will become apparent from the description of the drawings and the invention, which follow.

DESCRIPTION OF THE PREFERRED EMBODIMENTS

Figure 1:
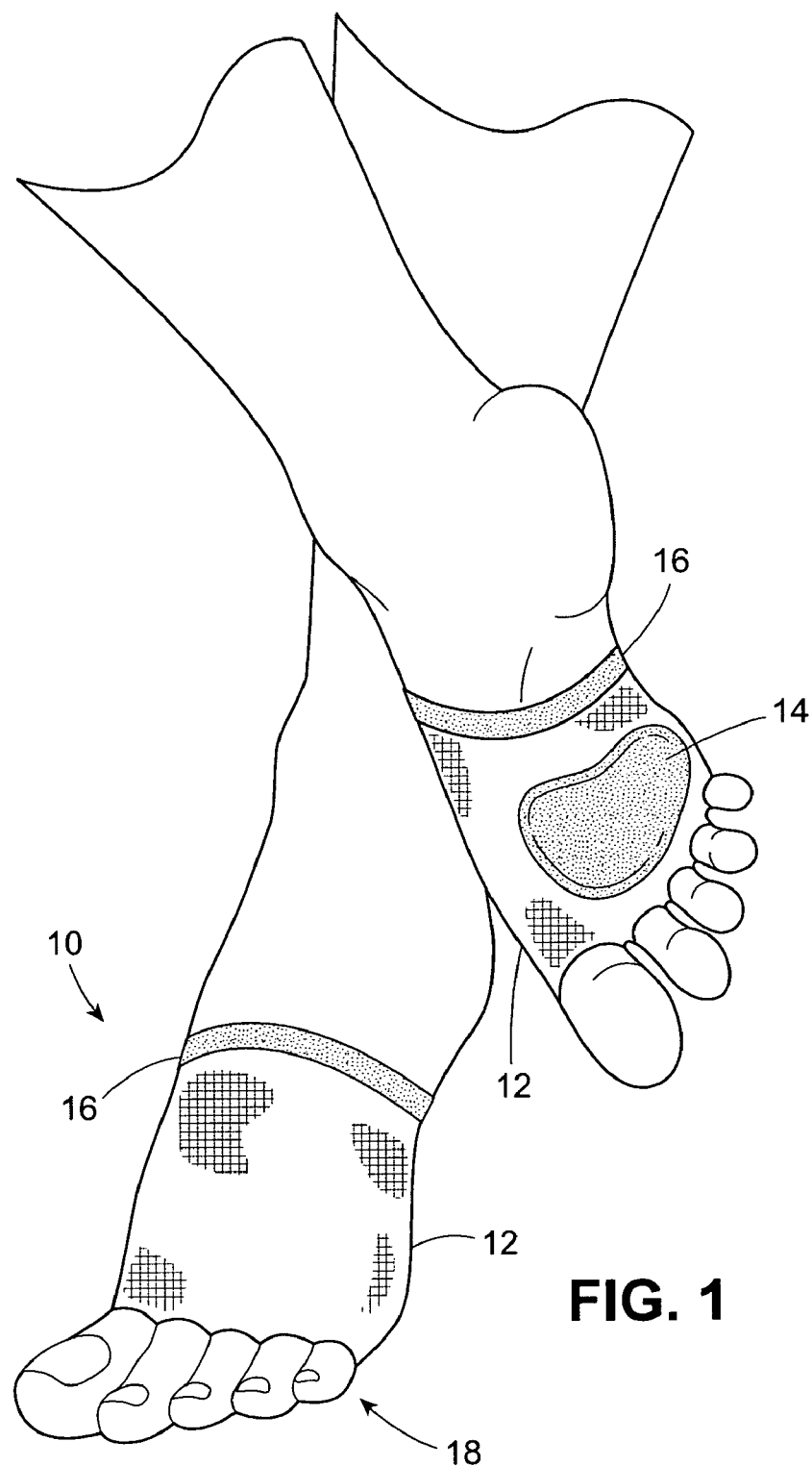
FIG. 1 is a perspective view of one embodiment of the formfitting protective footwear apparatus of the present invention.

In one embodiment, as shown in FIG. 1, the form fitting protective footwear apparatus 10 of the present invention comprises an elasticized sleeve 12 capable of remaining fitted about the forefoot and being provided with a footpad 14 of protective materials sufficient to protect the ball of the foot when apparatus 10 is in place over a human foot. Sleeve 12 of this embodiment of the invention is further provided with means 16 for retaining sleeve 12 about the instep of the foot and means 18 for retaining sleeve 12 at the forefoot without slippage toward the heel, e.g., holes for the toes.

Figure 2:
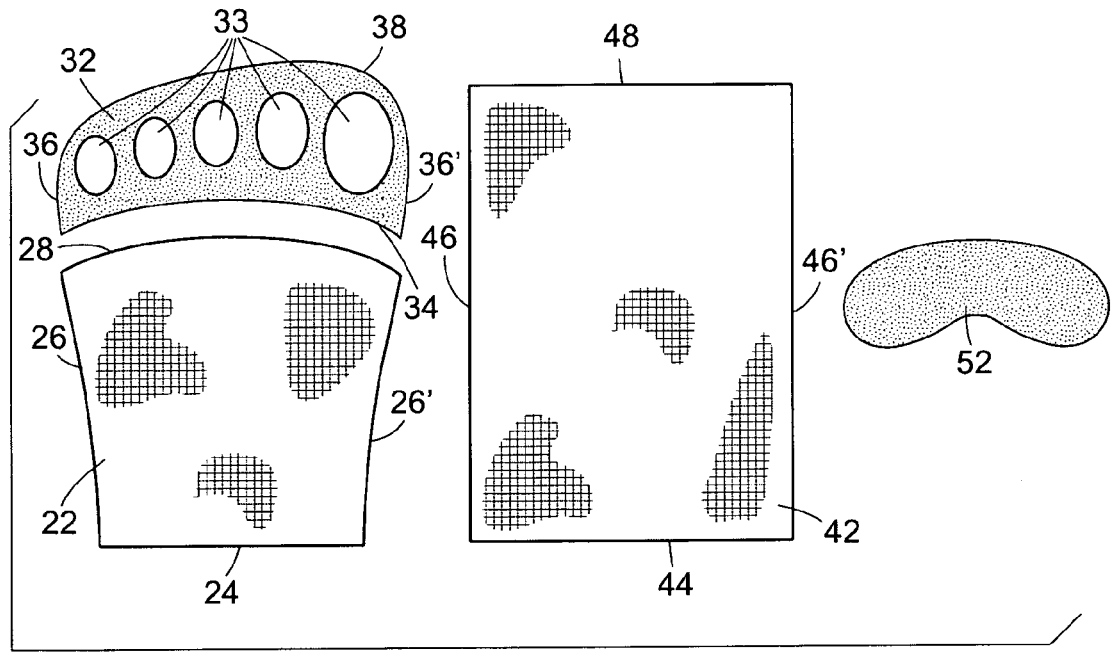
FIG. 2 shows the construction elements of a second embodiment of the present invention.

FIG. 2 shows the construction elements of a second embodiment of the present invention. As shown in FIG. 2, the embodiment shown is constructed of four elements. First element 22 is an upper elasticised element having a first edge 24 disposed perpendicularly to side edges 26 and 26' thereof and a second edge 28 defining a curve or an oblique angle such that the portions of second edge 28 proximate to side edges 26 and 26' are closer to first edge 24 than is the center portion of second edge 28. Second element 32 is a non-elasticised element having a first edge 34 defining a curve or angle that matingly corresponds with the angle or curve of second edge 28 of first element 22, side edges 36 and 36', and a second edge 38 provided with five toe holes 33 disposed adjacent thereto. It is desirable that element 32 be sturdy enough for the portions adjacent to or between toe holes 33 do not tear during intensive use, but that the material from which element 32 is constructed provides sufficient comfort to the foot as not to induce blistering or tearing of the skin adjacent to or between the toes. Third element 42 is a lower elasticised element having both a first edge 44 and a second edge 48 disposed perpendicularly to side edges 46 and 46' thereof. Finally, fourth element 52 is a non-elasticised element suitable for use as a pad capable of protecting the ball of the foot, while not inhibiting the movement of the wearer. In various embodiments, fourth element 52 may be constructed of any suitable material, including smooth leather, suede leather, synthetic leather, moldable polymers and elastomers, and other suitable material. In addition, it is understood that fourth element 52 may be textured, as by dimpling, forming ridges therein, forming grooves therein, or other means, such that fourth element 52 may provide enhanced traction when in contact with a substantially flat surface, such as a floor, or a sailboard or surfboard.

Figure 3:
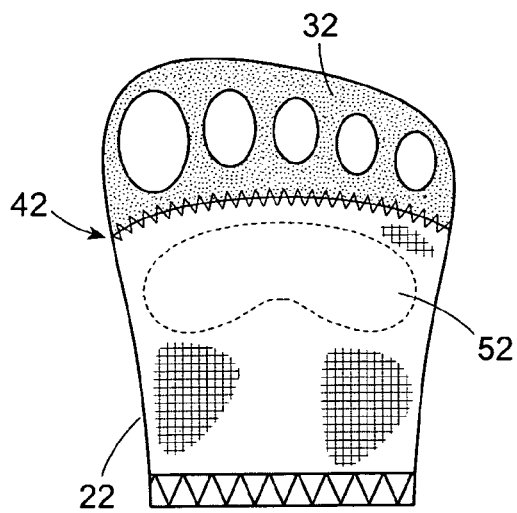
FIG. 3 shows a perspective view of the embodiment constructed from the elements shown in FIG. 2.
Figure 4:
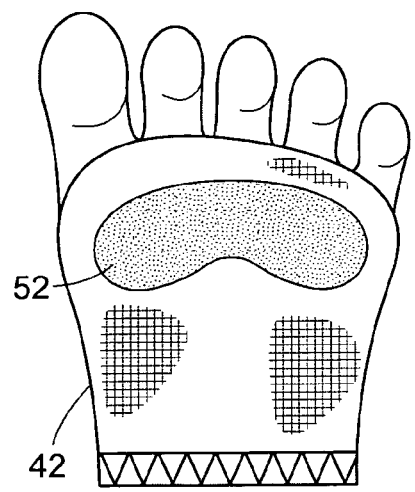
FIG. 4 shows a plan view of the embodiment of FIG. 3 positioned for use over a human foot.

To construct this embodiment, first and second elements 22 and 32 are joined, preferably by stitching, along their matingly corresponding edges 28 and 34. Next, fourth element 52 is joined to third element 42, again, preferably by stitching, such that fourth element 52 will be positioned under the ball of the foot in the finished article. First and third elements 22 and 42 are then joined to form a foot-shaped profile, again, preferably by stitching, along their side edges 26/45 and 26'/46', such that perpendicularly disposed second edges 24 and 44 of first element 22 and third element 42 are adjacent each other and in parallel, leaving an opening therebetween capable of accommodating the insertion of a foot into the void created between first and third elements 22 and 42. It is important to note that at this point, fourth element 52 should be disposed within the interior void created between first and third elements 22 and 42. First edge 38 of second element 32 is then joined to third element 42, again, preferably by stitching. Finally, the constructed article 20 is trimmed along the joined edges and turned inside-out, such that the trimmed edges now occupy the interior void and fourth element 52 is now disposed on the exterior of the article. FIG. 3 shows a perspective view of constructed article 20 made from the elements shown in FIG. 2 and FIG. 4 shows a plan view of the embodiment of FIG. 3 positioned for use over a human foot.

Figure 5:
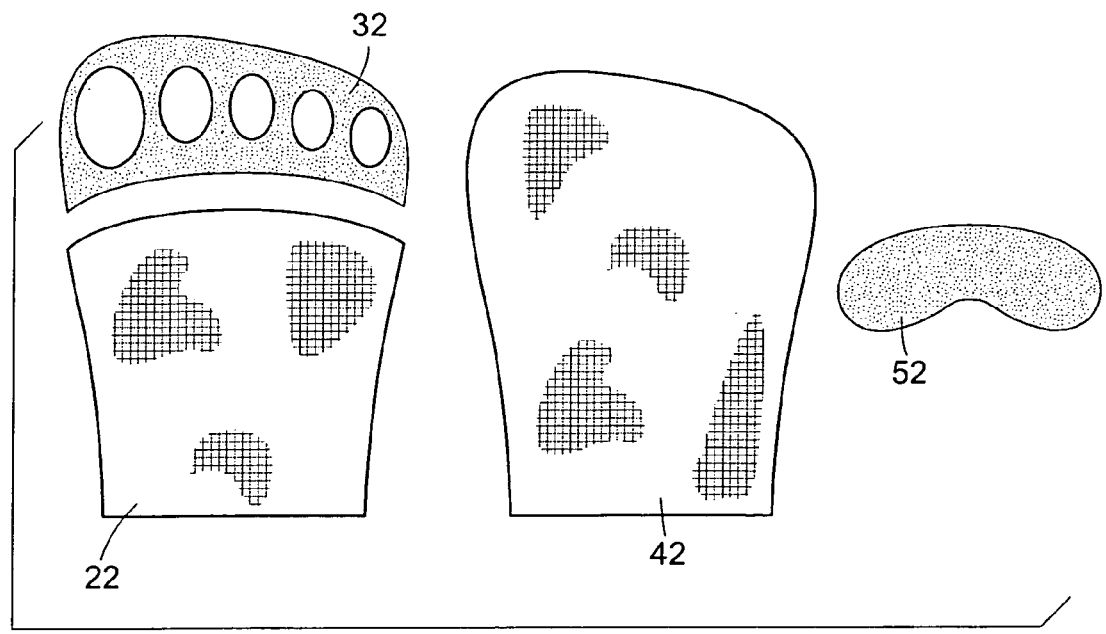
FIG. 5 shows the components of a third embodiment of the present invention.
Figures 6A, 6B:
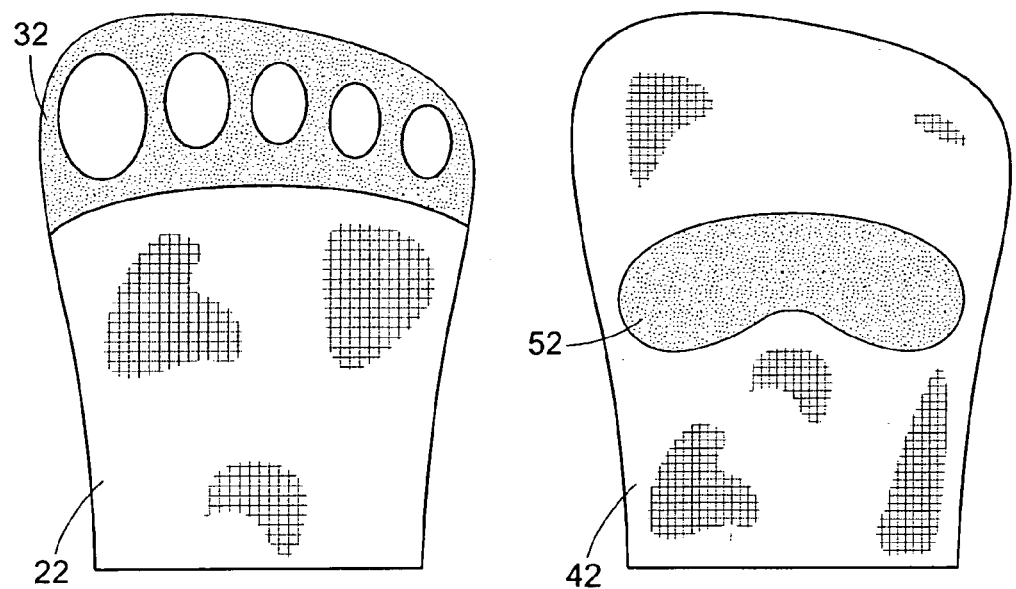
FIGS. 6A–B show top and bottom plan views of the finished assembly of the third embodiment of the present invention constructed from the components shown in FIG. 5.
Figure 7A:
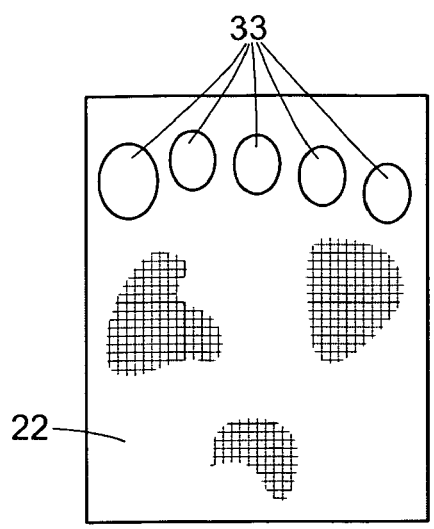
FIGS. 7A–E show a sequence illustrating the construction and assembly of a fourth embodiment of the present invention.
Figure 7C:
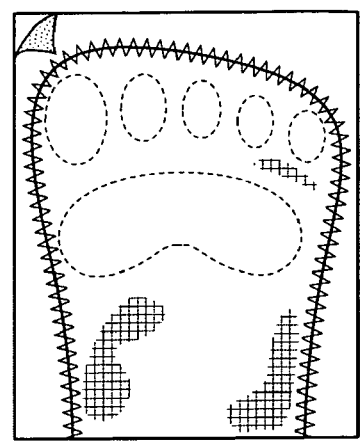
Figure 7D:
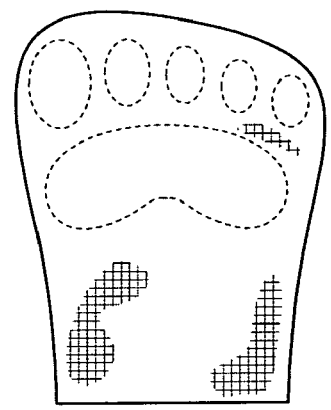
Figure 7B:
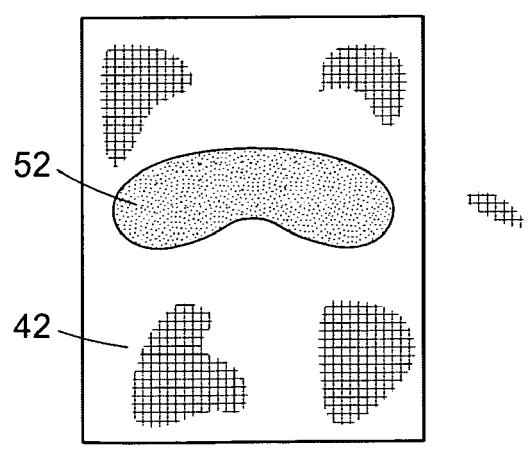
Figure 7E:
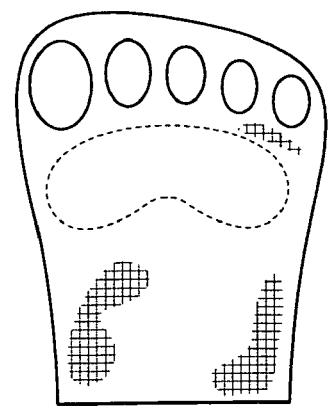
Figure 8:
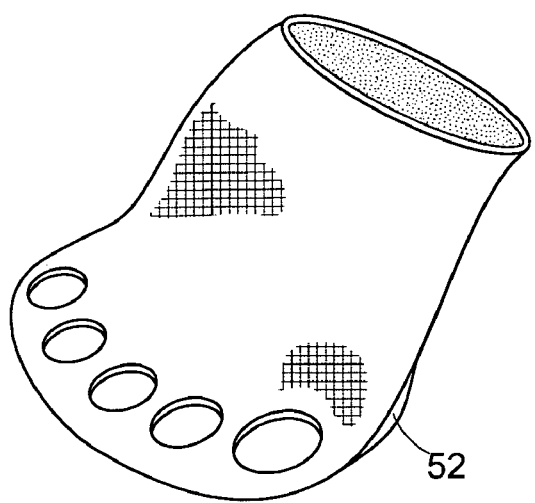
FIG. 8 shows a perspective view of the fourth embodiment constructed according to the sequence of FIGS. 7A–E.

It is understood that these steps may be performed in different sequences, provided that the finished article is properly constructed to withstand intensive use. In addition, it is understood that the components may be of different configurations, e.g., they may be pre-cut such that construction is completed without need for a trimming step. FIG. 5 shows how the components of a third embodiment of the present invention may be constructed. FIGS. 6A–B show top and bottom plan views of the finished assembly of the third embodiment of the present invention constructed from the components shown in FIGS. 5-A–C. Similarly, FIGS. 7A–E show a sequence illustrating the construction and assembly of a fourth embodiment of the present invention, wherein the upper element that accommodates the toe holes is of unitary construction. FIG. 8 shows a perspective view of the fourth embodiment constructed according to the sequence of FIGS. 7A–E.

Figure 9B:
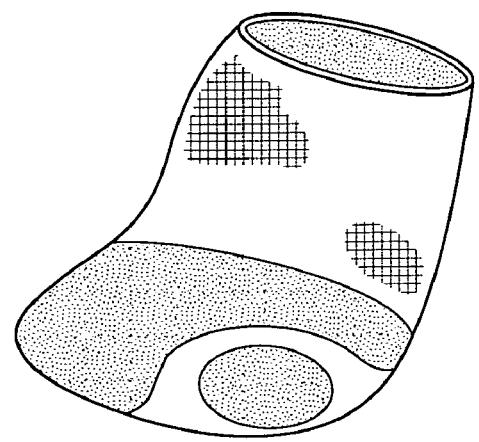
FIGS. 9A–B shows the components of a fifth embodiment of the present invention and the constructed embodiment, respectively.
Figure 9A:
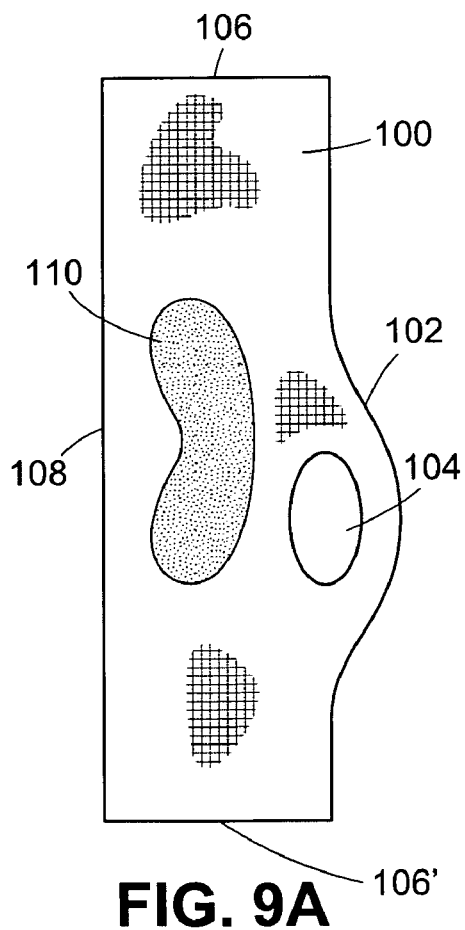

FIGS. 9A–B show the components of a fifth embodiment of the present invention and the constructed embodiment, respectively. As shown in FIG. 9A, this fifth embodiment is formed from an elongated strip of material 100 having first edge 102 defining an outward curve or angle such that a single toe hole 104 may be defined adjacent thereto, side edges 106 and 106', and second edge 108 that is substantially straight and disposed perpendicularly to each of side edges 106 and 106'. Footpad 110 is joined to elongated strip 100 adjacent toe hole 104, such that in the completed article the footpad is disposed in the area of the ball of the foot. Construction of this embodiment is achieved simply by sewing side edges 106 and 106' together, such that footpad 110 is disposed interiorly, and turning the finished article inside-out. In use, the article is slipped over a human foot such that the great toe is inserted into toe hole 104, the remaining toes extending unencumbered beyond first edge 102.

Figure 10:
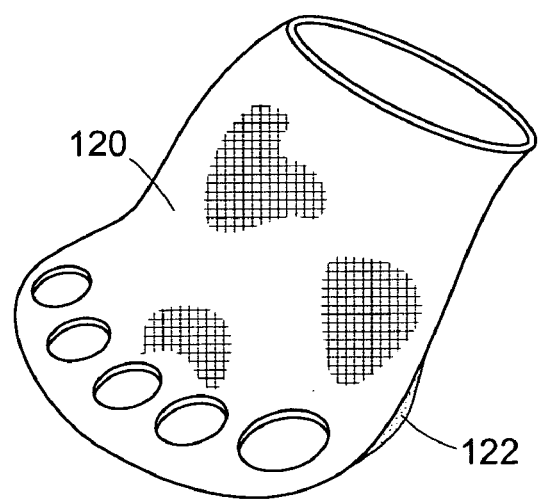
FIG. 10 shows a perspective view of a sixth embodiment of the present invention.
Figure 11A:
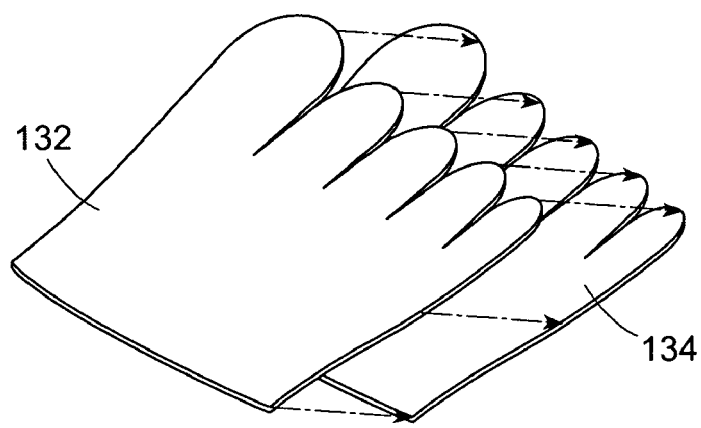
FIGS. 11A–D shows a sequence illustrating the construction and assembly of a seventh embodiment of the present invention.
Figure 11B:
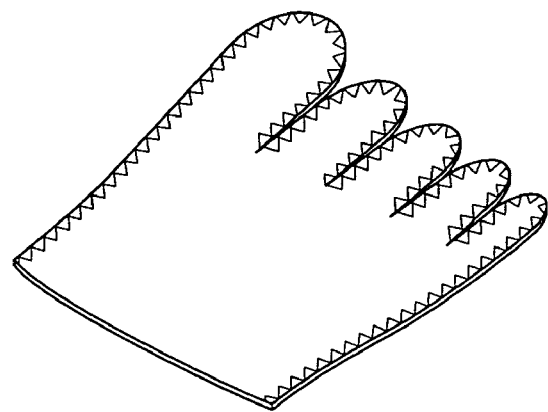
Figure 11C:
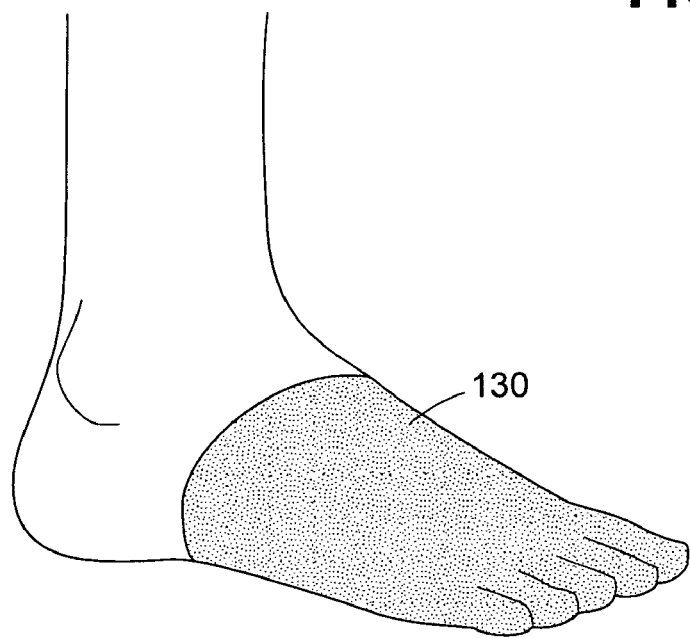
Figure 11D:
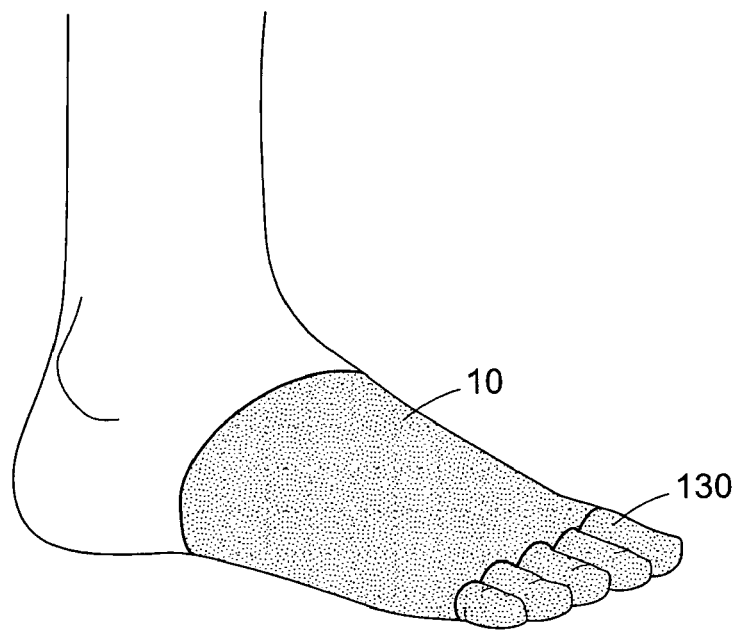

FIG. 10 shows a perspective view of a sixth embodiment of the present invention. This embodiment 120 is of unitary construction and is formed by a conventional molding process. Footpad 122 constructed of a like or alternate material may optionally be provided.

FIGS. 11A–D shows a sequence illustrating the construction and use of a seventh embodiment of the present invention comprising two elements. First element 130 is a thin half-sock provided with toe sleeves. First element 130 is constructed from matching elements 132 and 134 that are joined, preferably by stitching along their forwardmost edges. Second element 10 is any of the other embodiments of the present invention. In use, the wearer first slips element 130 over the foot, and then slips on article 10 of the present invention, such that the toes are protected from contact with the floor by element 130.

Figure 12:
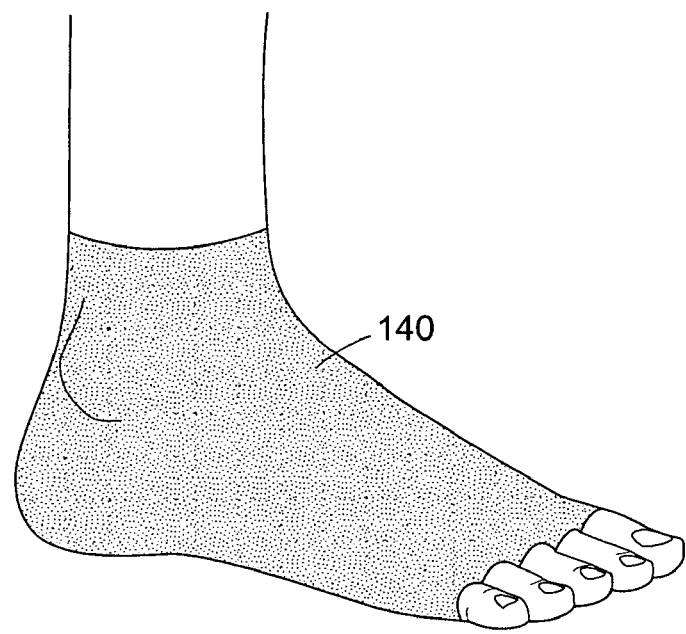
FIG. 12 shows a perspective view of an eighth embodiment of the present invention positioned for use over a human foot.

Finally, FIG. 12 shows a perspective view of an eighth embodiment 140 of the present invention positioned for use over a human foot. This embodiment, which may be adapted for use with any of the other embodiments of the invention, is characterized by its extension over the ankle, thereby providing increased lateral stability and support.

It is understood that the presently claimed invention may be embodied in other specified forms without departing from the spirit or essential characteristics thereof. The present embodiments are therefore to be considered in all respects as illustrative and not restrictive, and all changes which come within the meaning and range or equivalency of the claims are therefore intended to be embraced therein.

What is claimed is:

1. Formfitting footwear for dancers comprising:
a protective sleeve to be worn on a human foot comprising an inner portion and an outer portion;
toe openings disposed in said sleeve;
protective material disposed adjacent to said toe openings in said inner portion of said sleeve; and
a footpad disposed on said outer portion of said sleeve, wherein said protective material and said footpad are positioned on said sleeve in locations whereby they are underneath and protect a ball of said human's foot when inserted in said sleeve.

2. The footwear of claim 1, further comprising material which retains said sleeve about said foot's instep when inserted in said sleeve.

3. The footwear of claim 1, wherein said sleeve is formed from at least two sheets of material stitched together.

4. The footwear of claim 1, wherein said footpad is made from material which does not inhibit movement of a wearer.

5. The footwear of claim 4, wherein said footpad is made from a material from the group consisting of smooth leather, suede leather, synthetic leather, moldable polymers and elastomers.

6. The footwear of claim 1, wherein said footpad is textured to enhance traction.

7. The footwear of claim 6, wherein said textured footpad comprises one or more of the following: ridges, grooves and dimpling.

* * * * *